United States Patent [19]

Kleinberg et al.

[11] Patent Number: 4,820,506

[45] Date of Patent: Apr. 11, 1989

[54] SALIVARY STIMULANT

[75] Inventors: Israel Kleinberg, Smithtown; Leo M. Sreebny, East Setauket, both of N.Y.

[73] Assignee: Research Foundation, State University of New York, Albany, N.Y.

[21] Appl. No.: 45,618

[22] Filed: May 1, 1987

[51] Int. Cl.$^4$ ............................................. A01N 25/06
[52] U.S. Cl. ...................... 424/40; 424/493; 426/548; 426/650; 426/658
[58] Field of Search ............... 426/3, 72, 658, 548, 426/650; 424/40, 48, 49, 52, 81, 154, 435, 493, 104

[56] References Cited

U.S. PATENT DOCUMENTS

| | | | |
|---|---|---|---|
| 4,059,686 | 11/1977 | Tanaka et al. | 424/19 |
| 4,088,788 | 5/1978 | Ream et al. | 426/3 |
| 4,452,820 | 6/1984 | D'Amelia et al. | 426/3 |
| 4,472,437 | 9/1984 | Corsello et al. | 426/3 |
| 4,515,770 | 5/1985 | Besic | 424/49 |
| 4,537,689 | 8/1985 | Morrow et al. | 252/11 |
| 4,715,369 | 12/1987 | Suzuki et al. | 128/156 |
| 4,726,953 | 2/1988 | Carroll et al. | 426/5 |

*Primary Examiner*—Ellis P. Robinson
*Assistant Examiner*—P. J. Ryan
*Attorney, Agent, or Firm*—Lackenbach Siegel Marzullo & Aronson

[57] ABSTRACT

An aqueous liquid for promoting the production of human saliva in situ comprises:
 (a) about 2 to 3 wgt percent organic acidulent such as citric, malic, or ascorbic acid;
 (b) about 0.5 to 2.5 wgt percent of a natural, food-grade sweetener such as fructose or 0.05 to 0.5 wgt percent of a synthetic sweetener such as aspartame or saccharin; and
 (c) a saturated calcium phosphate solution.

The preferred form of the aqueous liquid is a metered, hand-actuated, aerosol spray of about 0.15 ml. per actuation.

By employing the aqueous liquid of the invention the production of saliva is tripled, thus alleviating the many symptoms of xerostomia no matter what its cause.

13 Claims, No Drawings

SALIVARY STIMULANT

FIELD OF THE INVENTION

This invention relates to xerostomia, or dry mouth. Low generation and flow of saliva in the mouth has several possible causes and substantial effects on taste, eating, digestion and teeth as well as leading to breath malodor, mucositis, sores on tongue, cheeks or lips, desiccation of lips, gingival problems, and microbial imbalance in the mouth. Therefore, stimulation of the generation and flow of saliva can be a great benefit to many people.

It is estimated that about ten percent of the population over 50 years of age and 25 percent of the population over 65 years of age suffer from xerostomia. The majority of those affected are women.

BACKGROUND OF THE INVENTION AND PRIOR ART

Some direct primary causes of xerostomia are autoimmune diseases such as Sjogren's syndrome, medical irradiation, malnutrition, hormonal imbalance, arthritis and perhaps aging. When areas of the head or neck are medically irradiated by as little as 1000 rads per week, 85 percent of the patients suffer from xerostomia after six weeks and 95 percent after three months.

Secondarily, xerostomia is a side effect from the administration of over 400 drugs, including major antihypertensives, antidepressants, antispasmodics, diuretics, muscle relaxants, antipsychotics, appetite depressants, and therapeutics for Parkinson's disease.

Furthermore, xerostomia may be emotionally induced by apprehension and fear, but postponed by lascivious anticipation. Breathing through the mouth may also induce xerostomia.

Normally an individual produces 0.5 to 1 liter per day of saliva. Although varying greatly between individuals, on average 65 percent of saliva is submandibular, 23 percent from the parotids, 8 percent from the minor mucous, and 4 percent sublingual. Saliva from the different sources have different proportions of electrolytes such as sodium, potassium, calcium, magnesium, chloride, bicarbonate, phosphate, nonelectrolytes such as urea and proteins. Upon stimulation, parotid contribution increases and thus proportionally, if not actually, submandibular decreases.

Food, in general, increases salivary flow. It has been known that the effects of secondary xerostomia may be broadly alleviated by sweet, sour, or bitter foods such as sweet candies, lemon drops, peppermint drops, chewing gum, and the like.

Direct sialogogues include:
- (a) pilocarpine compounds such as the hydrochloride, nitrate, or jaborandi leaves or their extracts;
- (b) neostigmine and its bromide, distigmine bromide (Ubretid), pyridostigmine bromide (Mestinon);
- (c) nicotinic acid, nicotinamide (Nicobion 500), and benzopyrone (Venalot); and
- (d) carbachol (Doryl), potassium iodide, and anetholthrithion (Sulfarlem S 25)

Indirect sialogogues include:
ascorbic acid (Vitamin C), citric acid tablets, malic acid, lemon glycerine swabs, and paraffin wax.

The above information has been reviewed by Imfeld in volume 13, number 4, of *Acta Parodontologics* at pp. 1083/111–10996/124 (1984) and by Vissink et al. at volume 129, number 43 of *Ned Tijdschrift Geneesked* at pp. 2054–2057 (1985).

Schlatter in U.S. Pat. No. 3,492,131 discloses a family of aspartylphenylalanine esters as synthetic sweeteners about 150 times sweeter than sucrose.

Morris et al. in U.S. Pat. No. 3,584,112 teach the use of sodium saccharin sweetener to mask the taste of dental plaque-tracing dye solution.

Krasse in "Caries Risk" chapter 8, Quintessence Publ. Co., Chicago, (1985) disclosed an acidulated calcium phosphate-xylitol tablet containing citric and malic acids to be masticated and swallowed each half minute in order to stimulate salivation. Differences in chewing habits would target different salivary glands in different people.

Goodman et al. in European patent application 1984—No. 128,654 have disclosed a new class of aminoacid based sweeteners: N-(L-aspartyl)-1,1 diaminoalkanes. Goodman's group in *Peptides*, pp. 549–554 (1984) also emphasize that the bitter taste receptors and sweet taste receptors in the mouth are closely allied, as are the molecular arrangement of "sweet" and "bitter" compounds. These same workers in The Journal of Medicinal Chemistry, volume 27, pp. 1668–1672 (1984) disclose the close relationship between the molecular structure of sweet and bitter trifluoroacetylaspartylanilides.

OBJECTS OF THE INVENTION

It is an object of the present invention to alleviate the symptoms and effects of xerostomia (dry mouth) by stimulating all the salivary glands (submandibular, parotid, sublingual and minor mucous) to produce more saliva simultaneously.

It is a further object of the invention to stimulate salivation cheaply, easily, and graciously without interference with the normal activities of everyday life.

It is yet a further object of the invention to stimulate salivation without burdening the user with any continuous mechanism or activity such as irrigation plates, chewing tablets or gums, repetitive rinsings, or topical application of organic compounds.

It is still another object of this invention to stimulate salivation with a minimum of interaction with human metabolism, that is avoiding the use of drugs or chemicals such as steroids, alkaloids, or aromatics which may have strong side effects or even be toxic in larger doses.

It is an additional object of the invention to stimulate salivation without harming or interacting with the teeth in any way. It is still a further object of the invention to stimulate salivation without swallowing large amounts of saliva or sialagogues.

It is another object of this invention to stimulate salivation by a means which has no psychological or emotional trauma involved.

Other objects of this invention will be appreciated by those skilled in the art.

SUMMARY OF THE INVENTION

The above and other objects of the invention are fulfilled by an aqueous liquid in bulk form or in the form of an atomized droplet colloidal spray comprising:
- (a) from about 2 wgt percent to about 3 wgt percent of a food-grade, organic acidulent:
- (b) from about 0.05 to about 0.5 wgt percent of a food-grade synthetic sweetener or 0.5 to about 25 wgt percent of a food-grade natural sweetener; and
- (c) a saturated calcium phosphate solution, whereby the production of all the salivary glands are promoted in the mouth without any corrosion, infection, mottling, discoloration, dissolution, or attack of either natural or prosthetic teeth.

The preferred form of the liquid is that of a metered, atomized, colloidal droplet spray of about 0.15 to 0.5 ml per handpump at a pH of about 3 to 4.

The preferred acidulants are citric, malic, and ascorbic acid of which citric acid is most preferred.

The preferred sweeteners are synthetic of which aspartylphenylalanine (Aspartame) and saccharin are most preferred.

The preferred forms of calcium phosphate are calcium monohydrogen phosphate (dibasic) or monocalcium dihydrogen phosphate (monobasic).

The preferred pH of either the liquid or the spray is from about 3 to about 4.

DESCRIPTION OF THE PREFERRED EMBODIMENTS

The onset of the effects of xerostomia is insidious with no clear line of demarcation when one has or has not the malady. Also different individuals may have different symptoms to a differing extent in a different succession. Dry mouth is the most common symptom. Alteration of taste sensation leads to change in the selection and perception of food. After alteration comes taste desensitation, which may lead to lack of any taste.

Sores on any of the mucous tissues of the oral area (tongue, gums, mouth, cheeks etc.), ulcerations, fissures, swellings, bleeding, coatings, even erosion of the tongue are all possible. With the decrease in saliva comes incomplete digestion, buildup of food, plaque, gingival hemorrhage, soreness at dental bridges, and extreme breath malodor. Also possible are swelling of various mouth tissues and possibly difficulty of speech. The lips may become desiccated or cracked. The rate of dental caries may increase dramatically.

One general approach to xerostomia is the use of synthetic saliva. There are many commercial brands, based on either pig mucin or carboxymethylcellulose (CMC), and including all the requisite electrolytes, buffer, and optional flavorants and/or sweeteners. The usual electrolytes are potassium, sodium, magnesium, calcium, chloride, bicarbonate, phosphate, and fluoride. Except for one Danish brand (Saliva-Orthana) and one Dutch experimental type based on mucin, most artificial salivas are based on CMC. Va-Oralube (First Texas Labs., Dallas) contains sorbital and fluoride in addition to the appropriate electrolytes and CMC. Moi-Stir (Kingswood Co., Toronto) has a high sodium content and is mint flavored. Salube (Oraphorm Co., Australia) comes in small dropper bottles. Saliment (Richmond Pharm. Co., Ontario), also based on CMC, is lemon flavored. Xero-lube (Scherer Labs., Dallas, Tex.), Artisial (Jouvenal, Paris, france), and Glandosane (Fresenius, Bad Homburg, West Germany) are available in ordinary spray bottles. Glycerine, hydroxyethylcellulose, and polyethylene oxides may also be found as bases for synthetic salivas.

Another broad approach to alleviating the manifold symptoms of xerostomia is to fit the mouth with a constant or controllable reservoir of synthetic saliva via a permanent or removable dental device. Palatal reservoirs require repeated refillings. A removable maxillary denture with reservoir rim is less cumbersome. It has several holes for filling with a syringe, drainage in use, and then washing after every meal. The removable denture with rim has space for about 3 ml of synthetic saliva. This denture, is expensive since custom-made, has an uncomfortable thickness, may hinder speech, and must be cleaned and refilled several times per day. J. A. Toljanic in Quintessence of Dental Technology, June 1985, pp. 355–358 and The Journal of Prosthetic Dentistry, volume 52, No. 4, pp. 540–544 shows pictures, gives directions, and has a bibliography on this subject.

Several strong compounds with metabolic effects, that is pharmaceuticals not foods, can stimulate production of saliva. These are generally administered in the form of tablets or capsules. They cannot be considered benign because unwanted side effects may occur. These compounds are cited in the Background section, above. Constant ingestion of these drugs cannot be prudently advised.

One can stimulate the production of saliva by more or less constant sucking of soft candies, hard drops, pastilles, ascorbic acid tablets, bonbons, small pastries, soft drinks, fruit juices, shredded coconut, and glasses of sweetened or acidulated water. This is cumbersome and can lead to a high rate of tooth decay.

Topical applications of glycerine, xylitol, carboxymethylcellulose, hydroxyethylcellulose, or other liquids or aqueous solutions of these compounds, which are more viscous than water, is preferable to repeatedly rinsing with water, because the higher viscosity of these humectants leads to less frequent applications.

The present invention is superior to all the other palatives and stimulants described above, because it stimulates all the salivary glands equally without the expense, bother, potential harm, or side effects of any of the known methods for alleviating xerostomia, no matter what the cause.

Firstly, the present invention utilizes a safe, mild, natural, food-acid of limited concentration which will give the resulting liquid a low enough pH to stimulate salivation. Food acids such as citric, lactic, malic, succinic, ascorbic, adipic, fumaric, and tartaric are preferred. Citric acid is most preferred.

Preferably the liquid or atomized spray of the present invention should be at a pH of from about 3 to about 4. This translates to a food-acid concentration from about 2 to about 3 wgt percent. The fruit acid stimulates the "sour" taste centers of the salivary system.

Secondly, a sweetener is employed in the solution or atomized spray of the present invention to stimulate salivation, yet it is known that the "sweet" centers are the same as the "bitter" centers of the salivary gland network of the mouth and tongue. The most common food-grade sweeteners are sugars such as glucose, dextrose, fructose, lactose, maltose, xylose, sucrose, corn sugar syrup, and other sweet mono- or di-saccharides. Ultimately, the word "sweet" is based on the taste sensations of professional taste panels. When a trained panel says is "sweet" is sweet. Normally, dilute solution of natural or synthetic compounds are further diluted and compared to very dilute solutions of sucrose. Then an arbitrary comparison such as "one-half" or "100 times" the sweetness of sucrose is given to the compound being tasted. Sucrose is the standard.

In the art of sialometry the stimulation by different sweeteners is measured by comparing the amount of resting flow and stimulated flow at equal times under equal conditions. In one such set of tests on healthy, young adults the normal resting flow was found to be 0.34 ml/min. The data for stimulated flow for citric acid, three natural sugars and two artificial sweeteners for six minutes are found in Table I, along with the projected time to return to resting flow rate:

TABLE I
Some Stimulated Flow Data for Salivation

| Stimulant | Molarity | Flow Rate (ml/min) | Return to Resting Flow Rate (min) |
|---|---|---|---|
| fructose | 0.29 | 0.57 | 6.8 |
| | 0.73 | 0.77 | 8.7 |
| | 1.17 | 0.97 | 8.7 |
| sucrose | 0.29 | 0.56 | 8.2 |
| | 0.73 | 0.67 | 7.7 |
| | 1.17 | 0.74 | 6.3 |
| glucose | 0.29 | 0.48 | 7.3 |
| | 0.73 | 0.43(sic) | 6.7 |
| | 1.17 | 0.52 | 6.7 |
| Aspartame | 0.002 | 0.52 | 5.7 |
| | 0.004 | 0.66 | 6.9 |
| | 0.008 | 0.70 | 6.9 |
| | 0.017 | 0.81 | 7.8 |
| | 0.034 | 0.82 | 6.8 |
| saccharin, sodium | 0.001 | 0.50 | 6.5 |
| | 0.002 | 0.54 | 6.8 |
| | 0.04 | 0.78 | 8.0 |
| | 0.08 | 0.87 | 8.7 |
| | 0.21 | 0.94 | 9.0 |
| | 0.42 | 1.04 | 10.5 |
| citric acid | 0.026 | 0.93 | 7.1 |
| | 0.052 | 1.13 | 7.2 |
| | 0.13 | 1.67 | 7.1 |
| | 0.26 | 1.68 | 7.3 |

The data shown in Table I permit several generalizations, especially when the accepted "sweetness value" of fructose 1.1 and glucose 0.7, compared to sucrose at 1.0, are considered. Increasing molarity of all six stimulants leads to increasing salivary flow rates. The increases for the three sugars were linear with concentration and followed the "sweetness value". The "sour" acid stimulant alone was twice as effective as the "sweet" stimulant alone, but the rate of increase for the "sour" and the artificial sweetness were asymptotic. Generally, the number of minutes for the return to the resting flow rate was about the same for all six stimulants.

The use of artificial sweeteners in the present invention is preferred over the use of saccharides because lesser concentrations are effective and the repeated use of sugars may cause dental caries in the patient. Sugars may be employed for edentulous individuals, however. The preferred concentration in the liquid or atomized spray of the present invention is from about 0.05 wgt percent to about 0.5 wgt percent for synthetic sweeteners, and 0.5 to about 25 wgt percent for sugars.

Certain commercial sweeteners are mixtures of both synthetic and natural compounds in order to overcome the aftertaste of synthetic sweeteners. It is believed that SWEET & LOW is a mixture of saccharin and dextrose (glucose) sugar, and that EQUAL is a mixture of ASPARTAME dipeptide and dextrose (glucose) or lactose. These mixtures are useful in practicing the present invention, even though the sugar content is potentially cariogenic. They do help overcome any unpleasant aftertaste. More preferable for the sweetener of the present invention is a synthetic sweetener containing a compound to overcome any unpleasant aftertaste, which is not cariogenic. Most preferable for this purpose is a synthetic sweetener plus a non-sugar, sugar-related compound (an alcohol sugar) such as sorbitol, xylitol, mannitol, maltilol, and hexitol, or starch hydrolysate such as Lycansin, or the like, of which sorbitol is most preferred. These and similar hydroxy compounds overcome any unpleasant aftertaste of synthetic sweeteners without being cariogenic.

In fact, there are many synthetic compounds much sweeter than sucrose, according to taste panels. Their general use is contemplated by this invention, especially if the compounds are cleared for human consumption by The U.S. Food and Drug Administration. Selected highly "sweet" synthetic compounds are illustrated, but not limited, by those found in Table II. The molecular structure of many other synthetic sweeteners will be known to those skilled in the art. In the present invention saccharin or Aspartame to which sorbitol or mannitol has been added is the preferred sweetener.

TABLE II
Sweetness Values of Some Synthetic Compounds

| Compound | "Sweetness" Times Sucrose |
|---|---|
| N—(L-aspartyl)-N'—[(2,2,5,5 tetramethylcyclopentyl)carbonyl]-(S)—1,1 diaminoethane | 600–800 |
| L-aspartyl-1,1-diaminodycyclopentyl-methane | 500–700 |
| L-aspartyl-1,1-diaminotetramethylcyclopentane | 800–1000 |
| L-aspartyl-1,1-diaminotetramethylcyclopentane, as the 1.5 hydrate | 600–800 |
| L-aspartyl-1,1-diaminodimethylcyclopentane | 300–400 |
| L-apartyl-1,1-diaminomethylcyclohexyl | 150–250 |
| tripeptides: Asp-D-Ala-1-amino-cycloalkane OCH3 where cycloalkane is $C_3$ to $C_6$ | 20 |
| trifluoroacetyl-L-aspartyl-p-cyanoanilide | 3000 |
| trifluoroacetyl-L-aspartyl-p-nitroanilde | 1500 |
| trifluoroacetyl-L-aspartyl-p-chloroanilide | 120 |
| L-aspartyl L phenylalanine methyl ester (Aspartame) | 160 |
| L-aspartyl-L-hexylalanine methyl ester | 225 |
| L-aspartyl-aminomalonic methyl fenchyl ester | 27000 |
| L-aspartyl-aminomalonic methyl trans-2-methyl cyclohexyl ester | 6400 |
| L-aspartyl-aminomalonic methyl cyclohexyl ester | 700 |
| ammonium 1,2-benzisothiazol-3-one (ammonium saccharin) | 500 |
| sodium 1,2-benzisothiazol-3-one (sodium saccharin) | 400 |

Because it is generally considered that a pH of 5.5 and below is potentially harmful to human teeth, in order to ensure stability of the teeth during long-term, repeated use of the liquid or atomized spray of the instant invention, the aqueous medium for the saliva stimulants is saturated calcium phosphate. This saturated solution by the general principles of aqueous equilibrium in chemistry minimizes any erosion, pitting, corrosion, or attack of the teeth by the salivary stimulant. There are at least five calcium phosphates: monocalcium phosphate $[CaH_4(PO_4)_2]$ dicalcium phosphate $[Ca_2H_2(PO_4)_2]$, octacalcium phosphate $[Ca_4(PO_4)_3OH]$, tricalcium phosphate $[Ca_3(PO_4)_2]$ and hydroxyapatite $[Ca_5(PO_4)_3OH]$. In aqueous solution all the possible ions will be in equilibrium with the relative amounts of the various ions determined by the pH. At the pH of about 3 to about 4 most favored for this invention, the calcium and phosphorus contents are about 0.6 wgt percent calcium and about 2.3 wgt percent phosphorus. Teeth kept in this saturated calcium phosphate solution will remain undamaged indefinitely. It is preferable to prepare the solution of the present invention with monocalcium phosphate, because it is moderately soluble in water and is often used as a supplement in foods. The liquid solution of the present invention may be carried and dispensed by a variety of means. It may be carried in any manner of bottle, flask, or container for alleviating xerostomia by drinking, rinsing, gargling, or topical application, all with or without expectoration. A flask of any size may be fitted with a hand-activated or bulb-activated spray pump for directing a stream into the mouth. Obviously, the finer the stream, the longer the supply will last. A means of pumping a fine stream into the mouth is preferable merely to using a bottle or flask as a liquid reservoir. It is most highly preferred to use a metering, hand-actuated, aerosol spray bottle for administration of an atomized colloidal droplet spray, because swallowing sialogogues should be minimized.

A so-called "atomizer" breaks up a stream or "shot" of liquid into a colloidal aerosol. This aerosol has such a high surface area that the colloid of liquid phase in air takes on the properties of a gas to some extent. That is, the colloidal aerosol stays suspended much longer than liquid drops would before falling. Furthermore, a colloidal aerosol will diffuse throughout a gaseous volume rather than coalesce in order to minimize its surface. For the present invention, an aerosol is ideal.

The atomized aerosol spray of the present invention may be hand-pumped through the properly small-sized orifice, sprayed under the pressure of gas such as air, carbon dioxide or isobutane, or be "atomized" by packaging under its own pressure. In any case, the colloidal droplets easily diffuse to all areas of the mouth to stimulate all the types and locales of salivary glands, for a minimal amount of stored liquid. The atomizer may be metered to deliver any desired amount of aerosol employing from about 0.05 to about 2 ml. The preferred amount of liquid to be transformed into an aerosol mist dose per actuation of the aerosol head is from about 0.1 to about 0.4 ml. The most preferred aerosol dose per actuation employs about 0.15 ml liquid stimulant.

An aerosol spray, especially a metered one, obviates any pain or trauma or effort by a seriously afflicted patient in chewing tablets, chewing gum, topically applying, rinsing or gargling, or expectorating. Many patients with xerostomia have sores, fissures, inflammation, desiccated or eroded areas, tumors, and the like for which an aerosol spray is the most benign means of contact to stimulate salivation. Even at one metered dose of aerosol a minute, a severely afflicted person could go about his affairs all day carrying a 50–75 ml aerosol container, easily carried in a pocket or purse.

Many other embodiments of the present invention are apparent to those skilled in the art. The protection sought for this invention by grant of Letters Patent is broadly described in the claims below:

We claim:

1. A composition for promoting the production of human saliva consisting essentially of an aqueous liquid solution of water having dissolved therein:

(a) from about 2 to about 3 wgt percent food-grade organic acidulent;

(b) a food-grade sweetener benign to stomic microflora selected from the group consisting of a sugar, a synthetic sweetener, and a reduced, sugar-related compound, and (c) a saturated calcium phosphate solution, whereby the production of human saliva is promoted in situ without corrosion, infection, or dissolution of human teeth.

2. The composition of claim 1, wherein the acidulent is selected from the group consisting of citric, malic, ascorbic, tartaric, fumaric, succinic, lactic, and adipic acids.

3. The composition of claim 1, wherein the sweetener is selected from the group consisting of fructose, glucose, dextrose, corn sugar, sucrose, lactose, maltose, xylose, aspartylphenylalanine ester, saccharin, aspartyldiaminoalkane, aspartylaminoalkyl carboxylic ester, trifluoroacetylaspartylanilide, aspartylalanyltripeptide, sorbitol, xylitol, mannitol, maltilol, dexitol, and hydrolyzed starch.

4. The composition of claim 3, wherein the sweetener is saccharin to which sorbitol has been added.

5. The composition of claim 3, wherein the sweetener is aspartylphenylalanine ester to which sorbitol has been added.

6. The composition of claim 3, wherein the sweetener is saccharin to which mannitol has been added.

7. The composition of claim 3, wherein the sweetener is aspartylphenylalanine ester to which mannitol has been added.

8. The composition of claim 1, wherein the calcium phosphate solution is selected from the group consisting of monocalcium, dicalcium, and tricalcium, and octacalcium phosphate, and hydroxyapatite.

9. The composition of claim 1, wherein the pH ranges from about 3 to about 4.

10. A composition for promoting the production of human saliva consisting essentially of an aqueous liquid solution of water in the form of an atomized droplet spray, having dissolved therein:

(a) from about 2 to about 3 wgt percent food-grade organic acidulent;

(b) a food-grade sweetener benign to stomic microflora selected from the group consisting of a sugar, a synthetic sweetener, and a reduced, sugar-related compound, and (c) a saturated calcium phosphate solution, whereby the production of human saliva is promoted in situ without corrosion, infection, or dissolution of human teeth.

11. The composition of claim 10, wherein the pH of the droplet spray ranges from about 3 to about 4.

12. The droplet spray of claim 10, wherein the spray is atomized and metered to deliver a dose of from about 0.1 to about 0.4 ml liquid per actuation.

13. The droplet spray of claim 12, wherein the dose is about 0.15 ml liquid per actuation.

* * * * *